United States Patent

Yoshida et al.

[11] Patent Number: 5,284,870
[45] Date of Patent: Feb. 8, 1994

[54] ALDOSE REDUCTASE INHIBITOR

[75] Inventors: Tadashi Yoshida, Osaka; Toshiyuki Kato, Kawanishi; Yoshimi Kawamura, Minoo; Koichi Matsumoto, Toyonaka; Hiroshi Itazaki, Takarazuka, all of Japan

[73] Assignee: Shionogi Seiyaku Kabushiki Kaisha, Osaka, Japan

[21] Appl. No.: 15,356

[22] Filed: Feb. 9, 1993

[30] Foreign Application Priority Data

Feb. 26, 1992 [JP] Japan .................................. 4-76140

[51] Int. Cl.$^5$ .................... A61 31/34; C07D 307/92; C07D 307/77; C12P 17/04
[52] U.S. Cl. ..................... 514/468; 435/126; 549/456; 549/458
[58] Field of Search ............ 549/456, 458, 468; 435/126

[56] References Cited

U.S. PATENT DOCUMENTS 4,797,417  1/1989  Okamoto et al. .

FOREIGN PATENT DOCUMENTS 0329361  8/1989  European Pat. Off. .
2219296  12/1989  United Kingdom .

OTHER PUBLICATIONS

Ganto Kagaku Ryoho 11(12) Part II, 2674–2680, 1984.
Derwent Publication Ltd., AN-89-036772/05, JP-A-6-3-310835 (1988).
Derwent Publication Ltd., AN-88-238170/34, JP-A-6-3-170392 (188).
J. Chem. Soc. Perkin. Trans. I., H. Arzeno, et al., pp. 2069–2076, 1984.
Chemical Abstracts. vol. 107, AN-115302y, M. V. Bhatt, et al. (1987).
Synthesis, pp. 713–716, Jun. 4, 1977, S. H. Ruetman.
Metabolism, vol. 34, No. 10, Oct. 1985, pp. 885–892, N. Simard-Duquesne, et al.
Derwent Publication Ltd., AN-88-231647/33, JP-A-6-3-165323 (1988).

Primary Examiner—Bernard Dentz
Attorney, Agent, or Firm—Oblon, Spivak, McClelland, Maier & Neustadt

[57] ABSTRACT

The present invention relates to an aldose reductase inhibitor represented by the formula:

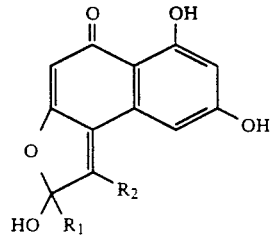

wherein $R_1$ is $(CH_2)_2COOH$ and $R_2$ is phenyl or p-hydroxyphenyl, or $R_1$ and $R_2$ are combined together to form a group of the formula:

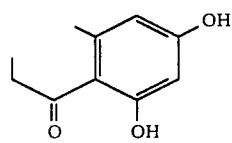

which was isolated from the fermentation products of *Chaetomella circinoseta* RF-3192.

3 Claims, No Drawings

ALDOSE REDUCTASE INHIBITOR

BACKGROUND OF THE INVENTION

1. Field of the Invention

The present invention relates to an aldose reductase inhibitor represented by the formula (I):

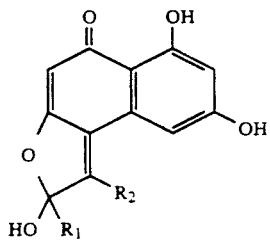

wherein $R_1$ is $(CH_2)_2COOH$ and $R_2$ is phenyl or p-hydroxyphenyl, or $R_1$ and $R_2$ are combined together to form a group of the formula:

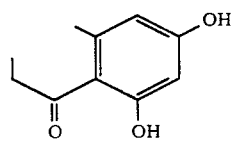

The present invention also relates to a microorganism producing said inhibitor and to a process for producing said inhibitor.

2. Related Art

The incidence rate of diabetes has hitherto increased and various complications thereof have become a quite serious problem. The diabetic complications may be caused by, for example, accumulation of polyol (e.g., sorbitol), free radical peroxidation, and glucosylation of proteins at the site of lysine residues. An inhibitor for aldose reductase (abbreviated hereinafter as AR) relating to polyol metabolism is expected to serve as a medicine for diabetic complications, that is, diseases arising from diabetes such as diabetic neuropathy, diabetic cataract, diabetic keratopathy, diabetic retinopathy, and diabetic nephropathy. So there have been many investigations into the development of such a medicine. Tolrestat represented by the following formula (II) (Simard-Duquesne, N. et al., Metabolism 34, 885–892, 1985) and WF-3681 represented by the following formula (III) (JP Kokoku No. 3-52458) are known as AR inhibitor. But AR inhibitor structurally similar to the compound of this invention is not known at all.

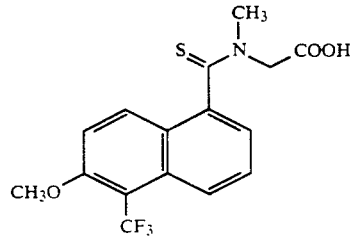

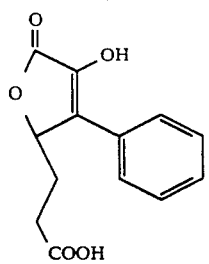

It has been revealed that AR as a rate-limiting enzyme in the metabolic pathway of polyol is present in blood vessels, peripheral nerves, lenses, retinae, and so forth, in which many diabetic complications often occur. Therefore, the significance of AR became understood in relation to diabetes. In the state of glycophilia such as diabetes, a larger amount of glucose than that of glucose capable of being metabolized in the glycolysis system is present in cells and the metabolism of glucose in the metabolic pathway of a polyol can readily be promoted because glucose is used as a substrate for AR. As a result, the abnormal accumulation of sorbitol is further enhanced. Sorbitol is a relatively stable substance; once the cells produce sorbitol, very little extracellular release of the sorbitol is found. The unbalance between the production and metabolism causes the intracellular accumulation of this sugar alcohol. This results in hypertonicity and osmotic uptake of water, thereby making it impossible to maintain the normal function of the cells and exhibiting a disorder of the cells. If the AR activity is inhibited, the abnormal intracellular accumulation of sorbitol can be avoided and the normal function of the cells can be maintained. Accordingly, the present inventors have made an effort to search compounds having an AR-inhibiting activity.

SUMMARY

In view of the above-mentioned matter, through the extensive study, the present inventors found the compound having AR-inhibiting activity in a culture medium of an imperfect fungus, *Chaetomella circinoseta* RF-3192. That is to say, they fermented said fungus, and extracted, isolated, and purified the compound to accomplish this invention. The present invention relates to a compound of the formula (I):

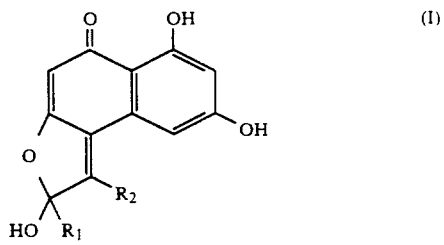

wherein $R_1$ is $(CH_2)_2COOH$ and $R_2$ is phenyl or p-hydroxyphenyl, or $R_1$ and $R_2$ are combined together to form a group of formula:

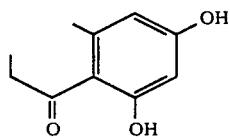

or the salt thereof.

Although the compound of this invention represented by the formula I can take tautomers (Ia)-(Ic) represented by the following formulas, the compound of the formula (I) is more stable than others. But it does not deny the existence of the other tautomers.

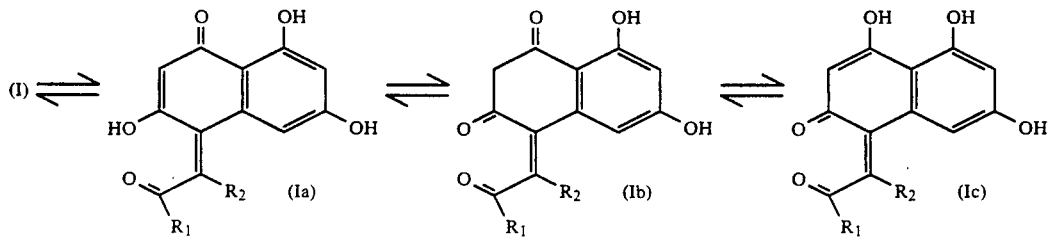

This invention further provides a microorganism producing the compound of this invention, which belongs to *Chaetomella circinoseta* and a process for producing the compound of this invention, which comprises the following steps:
cultivating the microorganism belonging to the genus Chaetomella and
isolating said compound from the culture medium.

The compound of the present invention may be used as a medicine for diabetic complications such as diabetic neuropathy, diabetic cataract, diabetic keratopathy, diabetic retinopathy, and diabetic nephropathy, because of its aldose reductase-inhibiting activity.

DESCRIPTION OF THE PREFERRED EMBODIMENTS

The strain RF-3192 belonging to *Chaetomella circinoseta* of this invention had the following properties.

Taxonomical Properties of the STrain RF-3192

Colonies of the strain on corn meal agar are flat, thin, and subhyaline to white, and on the surface of the agar dark brown to brownish black pycnidia are formed. The pycnidia with single raphe are ellipsoidal, 320–480 μm in length. The setae are septate, brown, not branching, and coiling at the apices (300–560×10–15 μm) or clavate (60–100×5–10 μm). The coiling setae at the apices are observed mainly at the parts of two poles of pycnidia and the clavate setae are observed at the middle part. The conidiophores are hyaline, filiform, irregularly branched, septate, and produce acropleurogenous conidia. The conidia are hyaline, aseptate, cymbiform to allantoid, and 7.5–10.5×1.5–2.0 μm in size.

The above-mentioned properties were compared with the description on the genus Chaetomella in "The Coelomycetes" by Brain C. Sutton (B. C. Sutton, The Coelomycetes, Commonwealth Mycological Institute, KEW, Surrey, England (1980)). As a result, the strain RF-3192 was identified as a strain of *Chaetomella circinoseta* Stork and named *Chaetomella circinoseta* RF-3192. The strain of this invention has been deposited with the Fermentation Research Institute Agency of Industrial Science and Technology at 1-3, Higashi 1-chome, Tsukubashi, Ibaraki-ken 305 as *Chaetomella circinoseta* RF-3192 with the accession No. FERM BP-3724 under the Budapest Treaty since Feb. 3, 1992.

The following is a general process for producing the compounds of this invention.

A strain belonging to the genus Chaetomella, for example, the above-mentioned *Chaetomella circinoseta* RF-3192 is cultivated with an ordinary medium composition and condition used for the conventional fermentation. The medium contains a carbon source, a nitrogen source, inorganic salts, and others in general. As occasion demands, vitamins and precursors may be added to the medium. The carbon source includes glucose, potato starch, dextrin, glycerol, sugars, organic acids, and the like, or the mixture thereof. The nitrogen source includes soybean powder, corn steep liquor, meat extract, yeast extract, cotton seed powder, peptone, wheat malt, ammonium sulfate, ammonium nitrate, and the like, or the mixture thereof. The inorganic salts include calcium carbonate, sodium chloride, potassium chloride, magnesium sulfate, cupric sulfate, manganese chloride, zinc sulfate, cobalt chloride, phosphates, and the like.

The cultivation is carried out at about 22°–about 37° C., preferably 26°–30° C. The cultivation time, which depends greatly upon the scale of the cultivation, is about 4–about 6 days for mass cultivation. In case of vigorous foaming, antifoam agents such as vegetable oil, lard, and polypropyleneglycol can be conveniently added to the medium before or during the cultivation.

After cultivation, the compounds of this invention can be recovered from the culture by the conventional methods usually used for recovering fermentation products, for example, filtration, centrifugation, absorption-elution or chromatography with use of various ion exchange resins or other active absorbents, extraction with use of various organic solvents, and the combination thereof.

The following will describe physicochemical properties and structures of the compounds RF-3192B, C, and A produced by the above process.

RF-3192B

1) Appearance: acidic, orange crystals
2) Melting Point: >230° C. (dec.)
3) IR, $\lambda_{max}^{KBr}$ cm$^{-1}$: 3304, 1701, 1646, 1608, 1574, 1378, 1248, 1219, 1204, 1165, 860, 851.
4) UV, $\nu_{max}$ (E$^{1\%}_{1\ cm}$) nm: in MeOH: 218sh(840), 265(350), 316(560), 410(170); in 0.01N HCl-90% MeOH: 218(690), 265(330), 317(520), 410(179); in 0.01N NaOH-90% MeOH: 240(580), 292(500), 318(440), 230sh(150), 460(120).
5) Elemental Analysis: Calcd. for $C_{21}H_{16}O_7+0.2\ CH_3COOC_2H_5$: C: 65.79, H: 4.46. Found: C: 65.41, H: 4.45.

6) SIMS: m/z 381 [M+H]+. HR-SIMS: m/z 381.0976 calcd. for $C_{21}H_{16}O_7+H$ (381.0974).

7) $^1$H-NMR (d$_6$-DMSO) ppm: 1.80–2.15 (2H, m), 2.24–2.35 (2H, m), 5.790 (1H, s), 6.255 (2H, s), 7.52–7.62 (5H, m), 8.186 (1H, OH, br), 10.393 (1H, OH, br), 12.177 (1H, OH, brs), 13.808 (1H, OH, s).

8) $^{13}$C-NMR (d$_6$-DMSO) ppm: 27.75 t, 31.64 t, 97.67 d, 103.89 d, 105.19 d, 107.35 s, 115.58 s, 123.94 s, 127.60 dx2, 129.35 dx2, 129.86 d, 130.54 s, 131.67 s, 152.56 s, 162.08 s, 163.62 s, 170.82 s, 173.45 s; 190.36 s.

9) Structure:

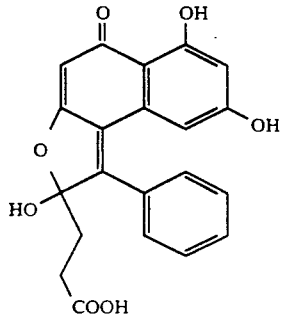

Although RF-3192B can take tautomers (IBa)–(IBc) represented by the following formulas, the compound of the formula (IB) is more stable than others.

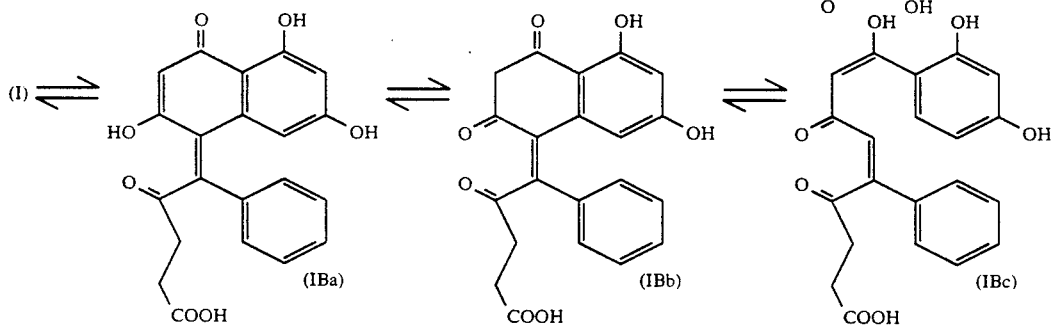

RF-3192C

1) Appearance: acidic, radish orange crystals
2) Melting Point: >150° C. (dec.)
3) IR, $\lambda_{max}^{KBr}$ cm$^{-1}$: 3394, 1653, 1608, 1470, 1416, 1383, 1359, 1319, 1280, 1233, 1215, 1169, 1123, 1100, 1044, 1018, 985, 842, 766.
4) UV, $\nu_{max}$ (E$^{1\%}_{1\ cm}$) nm: in MeOH; 220 sh(820), 273(500), 347(480), 440 sh(130); in 0.01N HCl-90% MeOH; 218(700), 273(460), 347(440), 440(130); in 0.01N NaOH-90% MeOH (irreversible shift): 238 sh(660), 265 sh(500), 297 sh(440), 318(460), 358 sh(340), 395 sh(190), 490 sh(50).

5) Elemental Analysis: Calcd. for $C_{20}H_{12}O_8$+C-H$_3$OH: C: 61.17, H: 3.91. Found: C: 61.73, H: 3.65.

6) SIMS: m/z 381 [M+H]+. HR-SIMS: m/z 381.0612 calcd. for $C_{20}H_{12}O_8+H$ (381.0610).

7) $^1$H-NMR (d$_6$-DMSO) ppm: 3.231 (1H, d, J=16.8), 3.408 (1H, d, J=16.8), 5.839 (1H, s), 6.364 (1H, d, J=2.2), 6.459 (1H, d, J=2.2), 7.099 (1H, J=2.0), 7.506 (1H, d, J=2.0), 10.712 (1H, OH, s), 11.339 (1H, OH, s), 12.568 (1H, OH, s), 13.857 (1H, OH, s).

8) $^{13}$C-NMR (d$_6$-DMSO) ppm: 49.60 t, 99.29 d, 105.10 d, 105.38 d, 107.90 s, 109.44 d, 109.50 s, 112.61 s, 122.05 s, 130.82 s, 135.10 s, 146.57 s, 162.88 s, 164.36 s, 165.20 s, 171.99 s, 190.26 s, 199.09 s.

9) Structure

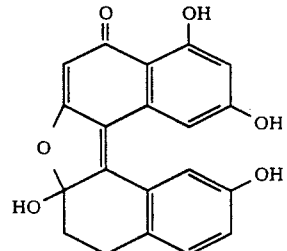

Although RF-3192C can take tautomers (ICa)–(ICd) and (IC') represented by the following formulas, the compound (IC) and it's antipode (IC') are more stable than others.

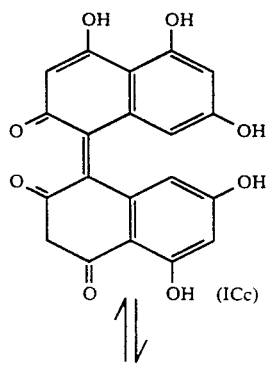

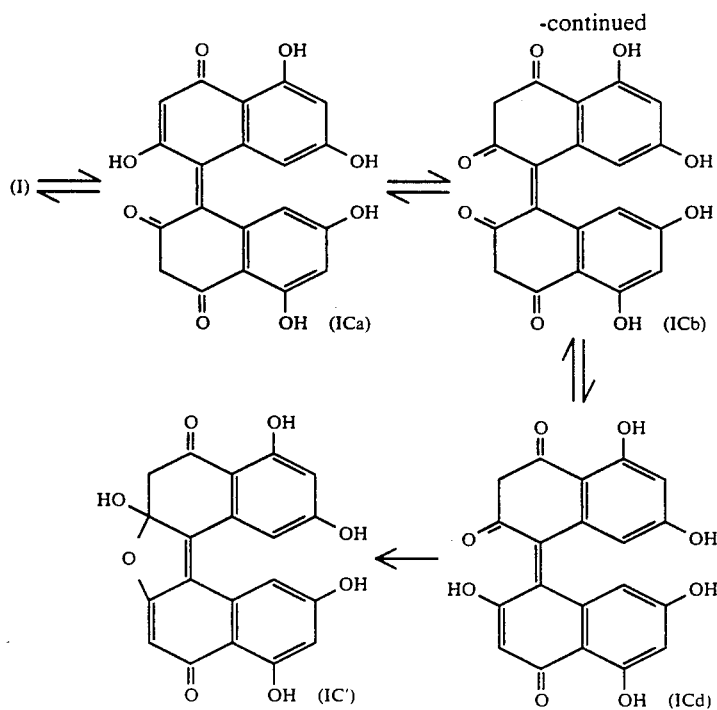
RF-3192A
1) SIMS: m/z 397 [M+1]⁺. HR-SIMS: m/z 397.0928 calcd. for $C_{21}H_{16}O_8+H$ (397.0923).
2) $^{13}$C-NMR (d$_6$-Acetone) ppm: 28.28 t, 33.01 t, 98.65 d, 104.85 d, 105.55 d, 109.29 s, 115.92 s, 123.38 s, 130.75 dx2, 117.06 dx2, 165.41 s, 124.58 s, 132.17 s, 152.92 s, 160.03 s, 162.72 s, 172.12 s, 173.77 s, 191.67 s.
3) Structure
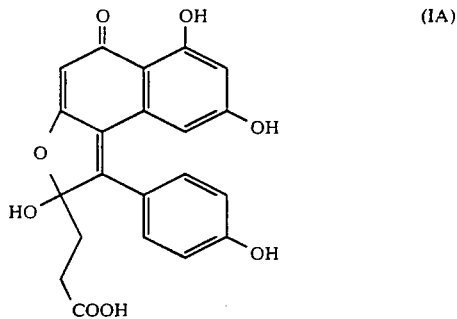
Although RF-3192A can take tautomers (IAa)–(IAc) represented by the following formulas, the compound (IA) is more stable than others.
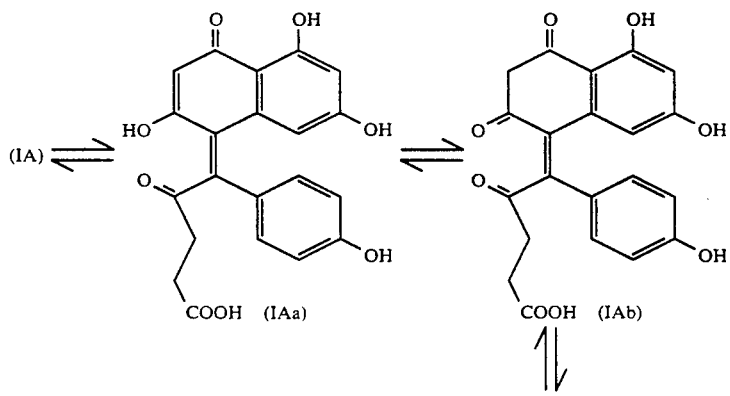

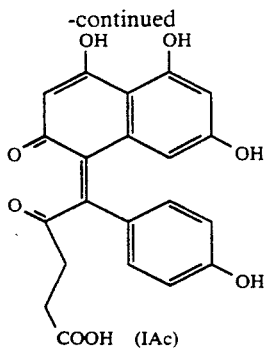

The present invention further provides an agent for inhibiting an aldose reductase, which comprises the compound of this invention.

A dose of the agent of this invention, which depends upon sex, age, and condition of a patient, is 1-1000 mg/day. The agent may be administered either orally or parenterally, but oral administration is recommended. For oral administration the agent can be used in pharmaceutical forms such as elixirs, capsules, granules, pills, suspension, emulsions, powders, tablets, syrups, and so on, but tablets are recommended.

The tablets can be prepared by the ordinary process of preparing tablets. Namely, the tablets are prepared either by direct compression of the compound of this invention with or without a vehicle, binder, and other suitable additives, or by compression of granules of the compound of this invention with suitable additives such as lubricant. The granules are prepared by compressing the compound of this invention with or without the above-mentioned additives and then crushing to granules, or by adding moistening agents to the compound, granulating, and drying. If necessary, coloring agents, flavoring agents, and so on may be added. The tablets may be coated with sucrose or other suitable coating agents.

The preferable embodiments of the present invention will be shown below as Example.

EXAMPLE

1. Culturing Step

A slant culture of the *Chaetomella circinoseta* RF-3192, which had been incubated at 28° C. for 10 days, was used to inoculate 2 L-Meyer flask charged with 800 ml of a medium containing 2.0% potato starch, 2.0% sucrose, and 0.5% yeast extract. The inoculated flask was subjected to a shake culture with stoke of 70 mm and 180 rpm at 28° C. for 3 days. The resulting culture (800 ml) was used to inoculate 300 L-jar fermenter charged with 20 L of the medium as described above and incubated with stirring and 150 rpm at 28° C. for 23 hours. Then, 12 L of the resulting culture was used to inoculate 500 L-tank charged with 300 L of a medium containing 2.0% soluble starch, 2.0% sucrose, and 0.5% yeast extract, and incubated with aeration of 300 L/min. and 350 rpm at 28° C. for 4 days.

2. Separating and Purifying Step (1) The culture (277 L) obtained in the above-mentioned step was adjusted to pH 9.0 with 5N sodium hydroxide, and then filtered. The filtrate was adjusted to pH 4.0 with hydrochloric acid and extracted with 126 L of ethyl acetate. The extract (85 L) was washed with 15 L of water, followed by evaporation, resulting in 45 g of residue. The residue was dissolved in 2 L of ethyl acetate and extracted twice with 400 ml of water adjusted to pH 8.0. The ethyl acetate phase was evaporated to give 14.36 g of crude product (crude-1). On the other hand, the water phase was adjusted to pH 4.0 with 2N hydrochloric acid, extracted twice with 800 ml of ethyl acetate, and then evaporated to give 19.38 g of crude product (crude-2).

(2) The separation and purification of activities, that is, RF-3192A, B, and C were performed by the following method.

a) Separation and Purification of RF-3192C

The crude product (crude-1) obtained in above (1) (14.36 g) was subjected to partition extraction with ethyl acetate and 0.5N sodium bicarbonate. The ethyl acetate phase was collected and the solvent was evaporated to give 13.44 g of crude extract. The crude extract was washed with hexane, and then 7.75 g of the resulting residue was subjected to column chromatography (column; $SiO_260(40-63\mu m)$, 150 g (Merck), solvent; acetone:dichloromethane = 4:6) to give 1.81 g of partially purified RF-3192C. The partially purified RF-3192C was further separated and purified by column chromatography (using the same column and solvent as above) to give 160 mg of purified RF-3192C. The purified RF-3192C was crystallized from dichloroethane to yield 117 mg of radish orange crystals of RF-3192C.

b) Separation and Purification of RF-3192B

After 0.5N sodium bicarbonate phase obtained by the partition extraction in above a) was adjusted to pH 2 with 2N hydrochloric acid the phase was extracted with ethyl acetate to give 1.175 g of crude extract. The crude extract was loaded onto a column (MCI GEL CHP-20P (75-150 $\mu m$), 300 ml (Mitsubishi Kasei Co.)), followed by gradient elution with (acetonitrile:tetrahydrofuran (THF) = 1:1):0.1% trifluoroacetic acid (TFA) = 3:7 to 8:2, resulting in 671 mg of partially purified RF-3192B. The partially purified RF-3192B was separated and purified by column chromatography (column; LiChroprep RP-18 (25-75 $\mu m$), 20$\phi$×500 mm (Merck), solvent; methanol:0.1% TFA = 1:1). The resulting purified RF-3192B (46 mg) was further separated and purified by column chromatography (column; LiChroprep RP-18 (25-75 $\mu m$), 20$\phi$×500 mm (Merck), solvent; (acetonitrile:THF = 1:1):0.1% TFA = 3:7) to give 37 mg of purified RF-3192B. The obtained purified RF-3192B was crystallized from ethyl acetate, and then washed with ether to yield 30 mg of orange crystals of RF-3192B.

RF-3192B was also obtained by the following procedures.

First, 19.38 g of the crude product (crude-2) obtained in above (1) was loaded onto a column (MCI GEL CHP-20P (75-150 μm), 300 ml (Mitusbishi Kasei Co.)), followed by gradient elution with (acetonitrile:THF=1:1):0.1% TFA=3:7 to 8:2, resulting in 4.03 g of crude product (crude A) and 926 mg of partially purified RF-3192B. Next, the partially purified RF-3192B was separated and purified by column chromatography (column; LiChropren RP-18 (25-75 μm), 20φ×500 mm (Merck), solvent; (acetonitrile:THF=1:1):0.1% TFA=3:7), and then the resulting purified RF-3192B (172 mg) was further separated and purified by column chromatography (column; LiChroprep RP-18 (25-75 μm), 20φ×500 mm (Merck), solvent; methanol:0.1% TFA=1:1) to give 46 mg of purified RF-3192B. Finally, the purified RF-3192B was crystallized from ethyl acetate, and washed with ether to yield 40 mg of orange crystals of RF-3192B.

c) Separation and Purification of RF-3192A

The crude product (crude A, 4.03 g) separated from the crude product (crude-2) in the above procedures was separated and purified by column chromatography (column; MCI GEL CHP-20P (75-150 μm), 300 ml (Mitsubishi Kasei Co.), solvent; (acetonitrile:THF=1:1):0.1% TFA=3:7) to give 1.088 g of partially purified RF-3192A. The partially purified RF-3192A was separated and purified by column chromatography (column; LiChroprep RP-18 (25-75 μm), 20φ×500 mm (Merck), solvent; acetonitrile:0.1% TFA=20:80) to give 45 mg of purified RF-3192A. The purified RF-3192A was further purified by column chromatography (column; LiChroprep RP-18 (25-75 μ), 20φ×500 mm (Merck), solvent; methanol:0.1% TFA=40:60), and the resulting purified product (39 mg) was purified again by column chromatography (column; LiChroprep RP-18 (25-75 μm), 20φ×500 mm (Merck), solvent; acetonitrile: 0.1% TFA=20:80) to give 10 mg purified product. However, the purified product was not perfectly pure. So the product was further purified by HPLC (column; COSMOSIL 5C18, 20φ×150 mm (NACALAI TESQUE, INC.), solvent; acetonitrile:0.1% TFA=20:80) to yield 6.7 mg of orange amorphous powder of RF-3192A.

3. Determination of the Structure

The structures of RF-3192A, B, and C which were isolated and purified in the above steps were determined.

The structures of RF-3192B and C were determined by subjecting their crystals to X ray analysis after RF-3192B was recrystallized from acetone and RF-3192C was from methanol. The determined structures were supported and confirmed by elemental analysis, mass spectrometric analysis, and NMR.

The structure of RF-3192A was determined by comparison between ¹H-NMR spectrums of RF-3192A and RF-3192B. Namely, in ¹H-NMR spectrum of RF-3192A there was AB-type quartet at 7.051 (2H, d, J=8.6) and 7.589 (2H, d, J=8.6) instead of a signal at 7.52-7.62 ppm (5H, m) originated from phenyl group of RF-3192B. Therefore, it was assumed that RF-3192A had p-hydroxyphenyl group instead of phenyl group of RF-3192B. From these results, the structure of RF-3192A was presumed, and the presumed structure was supported by molecular formula given from HR-SIMS.

RF-3192A, B, and C are racemic.

4. Aldose Reductase-Inhibiting Activity (1) Assay System for Aldose Reductase-Inhibiting Activity:

Using a homogenate of rat lenses as an enzyme source, glyceroaldehyde as a substrate, and NADPH as a coenzyme, the aldose reductase-inhibiting activity of the compounds of this invention was determined according to the method described in Abram N. Brubaker et al., J. Med. Chem. 29, 1094-1099, (1986).

Assay

To phosphate buffer containing 10 mM D, L-glyceroaldehyde, 0.4M $Li_2SO_4$, and aldose reductase inhibitor (RF-3192A, B, C, or a standard) was added the homogenate of rat lenses in triphosphopyridine nucleotide (reduced form) as an enzyme source so that the concentration of the homogenate was 0.1 mM. The change in absorbance at 340 nm for initial one minute was measured, and the inhibiting activity was determined.

The amount of the homogenate of rat lenses was such an amount as to give 0.200 ABS Unit/min. of the change in absorbance for initial one minute in the absence of the inhibitor.

Method for Preparing Homogenate of Rat Lenses

Lenses were removed from 20 eyeballs of rats and homogenized in 4 ml of 5 mM mercaptethanol using Glass-Teflon Homogenate. The obtained homogenate was centrifuged at 4° C. and 10,000 rpm for 20 minutes, and resulting supernatant was used as the enzyme source.

(2) Inhibiting Activity:

Tolrestat which is on the market in Italy and Ireland was used as a standard. The results of the assay were shown in Table 1.

TABLE 1

| Inhibitor | $Ic_{50}$ ng/ml (nM) | |
|---|---|---|
| RF-3192 A | 3.3 | (8.2 nM) |
| RF-3192 B | 1.6 | (4.2 nM) |
| RF-3192 C | 130 | (340 nM) |
| Tolrestat | 2.7 | (7.5 nM) |

We claim:

1. A compound of the formula (I):

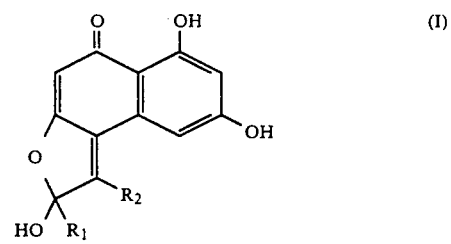

wherein $R_1$ is $(CH_2)_2COOH$ and $R_2$ is phenyl or p-hydroxyphenyl, or $R_1$ and $R_2$ are combined together to form a group of the formula:

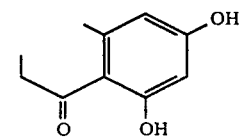

or the salt thereof.

2. A process for producing the compound of claim 1, which comprises the following steps:

cultivating a microorganism which belongs to the genus Chaetomella and produces said compound and isolating said compound from the culture medium.

3. A pharmaceutical composition comprising an effective amount of a compound of claim 1 in association with a pharmaceutically acceptable, substantially non-toxic carrier or excipient.

* * * * *

UNITED STATES PATENT AND TRADEMARK OFFICE
CERTIFICATE OF CORRECTION

PATENT NO. : 5,284,870
DATED : FEBRUARY 8, 1994
INVENTOR(S) : TADASHI YOSHIDA ET AL

It is certified that error appears in the above-identified patent and that said Letters Patent is hereby corrected as shown below:

Column 3, line 44, "the STrain" should read --the Strain--.

Column 11, line 31, "$\mu$), 20$\phi$ X 500" should read --$\mu$m), 20$\phi$ X 500--.

Signed and Sealed this

Seventh Day of March, 1995

Attest:

BRUCE LEHMAN

Attesting Officer          Commissioner of Patents and Trademarks